(12) United States Patent
Jallon (10) Patent No.: US 8,898,041 B2
(45) Date of Patent: Nov. 25, 2014

(54) SYSTEM AND METHOD FOR DETERMINING THE ACTIVITY OF A PERSON LYING DOWN

(75) Inventor: Pierre Jallon, Grenoble (FR)

(73) Assignee: Commissariat a l'Energie Atomique et aux Energies Alternatives, Grenoble (FR)

( * ) Notice: Subject to any disclaimer, the term of this patent is extended or adjusted under 35 U.S.C. 154(b) by 406 days.

(21) Appl. No.: 13/266,100

(22) PCT Filed: Apr. 26, 2010

(86) PCT No.: PCT/EP2010/055561
§ 371 (c)(1),
(2), (4) Date: Dec. 21, 2011

(87) PCT Pub. No.: WO2010/122173
PCT Pub. Date: Oct. 28, 2010

(65) Prior Publication Data

US 2012/0101785 A1 Apr. 26, 2012

(30) Foreign Application Priority Data

Apr. 24, 2009 (FR) ..................... 09 52691

(51) Int. Cl.
| | | |
|---|---|---|
| *G06F 7/60* | (2006.01) | |
| *G06F 17/10* | (2006.01) | |
| *A61B 5/11* | (2006.01) | |
| *A61B 5/00* | (2006.01) | |
| *G06K 9/00* | (2006.01) | |

(52) U.S. Cl.
CPC ............... *A61B 5/1116* (2013.01); *G06F 17/10* (2013.01); *A61B 5/1118* (2013.01); *A61B 5/1123* (2013.01); *A61B 5/4094* (2013.01); *A61B 5/4806* (2013.01); *G06K 9/00335* (2013.01); *A61B 5/7264* (2013.01)
USPC .......................................................... 703/2

(58) Field of Classification Search
CPC ... A61B 5/1116; G06K 9/00335; G06F 17/10
USPC .......................................................... 703/2
See application file for complete search history.

(56) References Cited

U.S. PATENT DOCUMENTS 7,421,369 B2 * 9/2008 Clarkson ...................... 702/150
7,558,622 B2 * 7/2009 Tran .............................. 600/509
(Continued)

FOREIGN PATENT DOCUMENTS

EP 1 731 097 A 12/2006
JP 2009 037410 A 2/2009

OTHER PUBLICATIONS

Bilmes, Jeff A. "A gentle tutorial of the EM algorithm and its application to parameter estimation for Gaussian mixture and hidden Markov models." International Computer Science Institute 4.510 (1998): 126.*

(Continued)

*Primary Examiner* — Aniss Chad
(74) *Attorney, Agent, or Firm* — Stroock & Stroock & Lavan LLP (57) ABSTRACT

The system for determining the activity of a person lying down has at least one motion sensor (CM) having at least one measurement axis, which is provided with a fastener (MF) for firmly connecting the motion sensor (CM) to a user. The system includes a filter (FILT) for selecting, for at least one measurement axis of the motion sensor (CM), a high-frequency signal (HF) and a low-frequency signal (BF); a first calculation unit (CALC1) for calculating a first variable (x(n)) representing a temporal variation of the low-frequency signal (BF); a second calculation means (CALC2) for calculating a second variable (y(n)) comprising the Euclidean norm, along at least one measurement axis, of the high-frequency signal (HF); and an analysis unit (AN) that determines an activity of prone user as a function of time using a hidden Markov model having N states corresponding to N activities respectively. The analysis unit (AN) also combines conjoint probability density functions of the first and second variables, said probability density functions being defined for each state of the model in question; and probabilities of transitions between two successive states.

15 Claims, 2 Drawing Sheets

(56) References Cited

U.S. PATENT DOCUMENTS

| | | | |
|---|---|---|---|
| 8,108,036 B2 * | 1/2012 | Tran | 600/509 |
| 8,403,865 B2 * | 3/2013 | Halperin et al. | 600/584 |
| 8,585,607 B2 * | 11/2013 | Klap et al. | 600/534 |
| 8,603,010 B2 * | 12/2013 | Lange et al. | 600/584 |
| 2008/0162088 A1 | 7/2008 | DeVaul et al. | |
| 2008/0275349 A1 | 11/2008 | Halperin et al. | |
| 2010/0079291 A1 * | 4/2010 | Kroll et al. | 340/573.1 |
| 2012/0143094 A1 * | 6/2012 | Jallon | 600/595 |

OTHER PUBLICATIONS

Borza, Paul-Valentin. Motion-based Gesture Recognition with an Accelerometer. Diss. Master's thesis, Babes-Bolyai University, Faculty of Mathematics and Computer Science, 2008.*

Jallon P et al: "Detection system of motor epileptic seizures through motion analysis with 3D accelerometers" Engineering in Medicine and Biology Society, Sep. 2009.

International Search Report and Written Opinion dated May 8, 2010, issued in counterpart International Application No. PCT/EP2010/055561.

* cited by examiner

SYSTEM AND METHOD FOR DETERMINING THE ACTIVITY OF A PERSON LYING DOWN

CROSS-REFERENCE TO RELATED APPLICATIONS

This application is a national phase application under §371 of PCT/EP2010/055561, filed Apr. 26, 2010, which claims priority to French Patent Application No. 0952691, filed Apr. 24, 2009 both of which are incorporated herein by reference.

BACKGROUND

1. Field of the Invention

The present invention relates to a system and to a method for determining the activity of a person lying down.

2. Description of the Related Art

Systems and methods for motion analysis based on hidden Markov models are known, such as those described for example in the documents "Gesture recognition using the XWand" by Daniel Wilson and Andy Wilson and "Motion-based gesture recognition with an accelerometer" (bachelor's thesis) by P. V. Borza.

The document "A hidden Markov model-based stride segmentation technique applied to equine inertial sensor trunk movement data", Journal of Biomechanics 41 (2008), 216-220 by Thilo Pfau, Marta Ferrari, Kevin Parsons and Alan Wilson relates to analysis of driving by horses.

An object of the invention is to allow the activity of a person lying down to be determined.

According to one aspect of the invention, a system is proposed for determining the activity of a person lying down, comprising at least two processing pathways of signals at the output of at least one motion sensor substantially affixed to said person, wherein a first of said at least two processing pathways processes a first component comprising signals of low frequencies and a second processing pathway processes a second component of signals of high frequencies, in which the system further comprises:
  first calculation means for calculating a first variable (x(n)) representing a temporal variation of said first component, for at least an axis of said motion sensor;
  second calculation means for calculating a second variable (y(n)) comprising the Euclidean norm, along at least one measurement axis, of said second component; and
  analysis means configured for determining an activity of said person as a function of time using a hidden Markov model having N states corresponding to N activities respectively,
  said analysis means being configured for combining:
  conjoint probability density functions of said first and second variables, said probability density functions being defined for each state of the model in question; and
  probabilities of transitions between two successive states.

According to a preferred embodiment, the probability density functions associated with each state comprise the product of at least one first probability density function of said first variable multiplied by at least one second probability density function associated with said second variable.

It is noted that a hidden Markov model can be defined by two random processes: a first process, which in the present application is called "state" and is not observed, or in other words is hidden, and a second process which is the observation, the probability density function of which at a given instant depends on the value of the state at the same instant. According to this aspect of the invention, the state can take discrete values.

Such a system enables the activity of a person lying down to be determined accurately and at low cost.

In one embodiment, a conjoint probability density function comprises a product of at least one probability density function for obtaining the first variable and of at least one probability density function for obtaining the second variable, said probability density functions being defined by the following expressions:

$$\begin{cases} P_{BF}(x(n)) = \dfrac{1}{\sqrt{2\pi}\,\sigma_x} \cdot e^{-\frac{x^2}{2\sigma_x^2}} \\ P_{HF}(y(n)) = \dfrac{1}{\sqrt{2^k}\,\sigma_y^k\,\Gamma\!\left(\dfrac{k}{2}\right)}\, y(n)^{\frac{k}{2}-1} e^{-\frac{y(n)}{2\sigma_y^2}} \end{cases}$$

in which:
$P_{BF}(x)$ is the probability density function of the first variable x corresponding to the state in question;
$P_{HF}(y)$ is the probability density function of the second variable y corresponding to the state in question;
k represents the degree of freedom of the high-frequency component equal to the number of measurement axes taken into account by said motion sensor;
$\sigma_x$ represents the square root of the variance of the first variable x, in the state of the hidden Markov model in question;
$\sigma_y$ represents the square root of the variance of the second variable y in the state of the hidden Markov model in Question; and
$\Gamma$ is the gamma function satisfying $$\Gamma\!\left(\frac{1}{2}\right) = \sqrt{\pi},\ \Gamma(1) = 1$$

and $$\Gamma\!\left(n + 1 + \frac{1}{2}\right) = n\Gamma\!\left(n + \frac{1}{2}\right).$$

Thus, for each state i, probability density functions $P_{x,i}(n)$ and $P_{y,i}(n)$, can be defined such that:

$$\begin{cases} P_{x,i}(x(n)) = \dfrac{1}{\sqrt{2\pi}\,\sigma_x} \cdot e^{-\frac{x(n)^2}{2\sigma_{x,i}^2}} \\ P_{y,i}(y(n)) = \dfrac{1}{\sqrt{2^k}\,\sigma_{y,i}^k\,\Gamma\!\left(\dfrac{k}{2}\right)}\, y(n)^{\frac{k}{2}-1} e^{-\frac{y(n)}{2\sigma_{y,i}^2}} \end{cases}$$

$\sigma_{y,i}$ being a quantity proportional to the time average of the variable y(n) in the state i. For example, $\sigma_{y,i}$ is the time average of the variable y(n) divided by k.

Thus, the real probability density functions of the observed signals can be approximated by probability density functions generally tailored to most movements.

In one embodiment, said analysis means are suitable for determining an activity of the lying-down user as a function of time using a hidden Markov model in at most five states chosen from a rest activity, a slight agitation activity, a trembling activity, a moderate agitation activity and a strong agitation activity.

Such a system serves to analyze the activity of a mobile element with improved accuracy. This is because by taking into account the high-frequency component it is possible to use additional information that enables small movements of the sensor, or in other words oscillations or vibrations, such as trembling, to be detected.

According to one embodiment, said analysis means are suitable for determining an activity of the lying-down user from a set of predetermined pairs of values of first and second variances, defining movement classes.

Thus, the non-observed process or state of the hidden Markov model can be a discrete $1^{st}$-order Markov process taking values in the set $\{0, 1, 2, 3, 4\}$. It can be characterized by the probabilities of transitions from one state to another: $P(\text{State}=j|\text{State}=i)$.

The observed process of the hidden Markov model is the multidimensional signal $(x(n),y(n))$, the conjoint probability density function of which depends on the state (the hidden process) at a given instant. Thus, for each state, the conjoint probability density function of the observed signal can be defined by the following equation:

$$P(x(n), y(n)|\text{State} = i) = P_{iState}(x(n)),$$

$$y(n)) = \sum_{n=0}^{n_{max}} \sum_{m=0}^{m_{max}} \alpha_{iState,m+(m_{max}+1)n} P_{x(\sigma_x[m])}(x(n)) P_{y(\sigma_y[n])}(y(n))$$

in which $\alpha_{iState,j}$ is a weighting coefficient enabling a state to be modeled by a plurality of elementary movements. This determination coefficient can be determined experimentally. $P_{iState}(x,y)$, also denoted by $P_i(x(n),y(n))$ represents the probability density function associated with the state i at the instant n, of $x(n)$ and $y(n)$. It comprises the product of the probability density functions $P_{x,i}(x(n))$ and $P_{y,i}(y(n))$ defined above.

If a set of observed data $\theta(n)$ is considered, combining the observed data $x(n)$ and $y(n)$, the following expression may be written:

$$P_i(x(n),y(n))=Pi(\theta(n)=p(\theta(n)/E(n)=i),$$

with $E(n)$ representing the state at the instant n.

Since $P(x,y|\text{State}=i)$ is a probability density function, the following condition is preferably met by the weighting coefficients:

$$\sum_{n=0}^{n_{max}} \sum_{m=0}^{m_{max}} \alpha_{iState,m+(m_{max}+1)n} = 1.$$

Using such classes it is possible to define, for each pair of movement classes, an elementary movement. One state of the model can therefore be described by a number of elementary movements.

In one embodiment, said pairs of values of first and second variances are suitable for satisfying the following conditions:

$$\begin{cases} n \in [0; n_{max}] \\ m \in [(0; m)_{max}] \\ n_{max} \leq 10 \\ m_{max} \leq 10 \\ n_{max} \times m_{max} \geq 6. \end{cases}$$

Thus, the number of defined elementary movements makes it possible to describe most movements of a person lying down and remains small enough to allow processing in real time.

In one embodiment, said movement classes are eighteen in number and are defined by:

$\sigma_x[0]=5\times10^{-3}$, $\sigma_x[1]=1.8\times10^{-2}$, $\sigma_x[2]=3.5\times10^{-2}$, $\sigma_x[3]=5.5\times10^{-2}$, $\sigma_x[4]=8\times10^{-2}$, $\sigma_x[5]=1\times10^{-1}$, $\sigma_y[0]=1\times10^{-2}$, $\sigma_y[1]=3\times10^{-2}$ and $\sigma_y[2]=8\times10^{-2}$.

These values are particularly well suited for determining the activity of a person lying down.

According to one embodiment, said real coefficients are defined by the following table:

| | iState | | | | |
| --- | --- | --- | --- | --- | --- |
| Class | 1State (rest) | 2State (slight agitation) | 3State (trembling) | 4State (moderate agitation) | 5State (strong agitation) |
| 0 | 0.2564 | 0 | 0 | 0 | 0 |
| 1 | 0.0513 | 0.0526 | 0 | 0 | 0 |
| 2 | 0.02564 | 0 | 0.04 | 0 | 0 |
| 3 | 0.2564 | 0.1579 | 0.04 | 0 | 0 |
| 4 | 0.0513 | 0.2632 | 0.16 | 0 | 0 |
| 5 | 0 | 0.0526 | 0.20 | 0 | 0 |
| 6 | 0.2564 | 0.1579 | 0.04 | 0 | 0 |
| 7 | 0.0513 | 0.2632 | 0.16 | 0.0926 | 0 |
| 8 | 0 | 0.0526 | 0.20 | 0.0926 | 0 |
| 9 | 0.0256 | 0 | 0 | 0.0370 | 0 |
| 10 | 0 | 0 | 0 | 0.1852 | 0 |
| 11 | 0 | 0 | 0.16 | 0.1852 | 0 |
| 12 | 0.0256 | 0 | 0 | 0.037 | 0.0556 |
| 13 | 0 | 0 | 0 | 0.1852 | 0.0556 |
| 14 | 0 | 0 | 0 | 0.1852 | 0.0556 |
| 15 | 0 | 0 | 0 | 0 | 0.2778 |
| 16 | 0 | 0 | 0 | 0 | 0.2778 |
| 17 | 0 | 0 | 0 | 0 | 0.2778 |

These values are particularly well suited for determining the activity of a person lying down.

At each instant n, it is then possible to determine a state of the person, knowing $P_i(x(n),y(n))$ by the expression:

$$E(n)=\arg_i\max(P_{x,i}(x(n))P_{y,i}(y(n))=\arg_i\max(P_i(x(n),y(n))),$$

in which the function arg max represents the maximum argument.

If the person at the instant n is at the state i, then $E(n)=i$.

However, it is generally not satisfactory to determine the state $E(n)$ at the instant n solely from the observed data, $x(n)$ and $y(n)$, and from the associated probability density functions $P_{x,i}(x(n))$ and $P_{y,i}(y(n))$ associated with these data respectively.

Experience has shown that it is desirable to take into account a priori, a state, for example the state $E(n-1)$ determined during the instant $n-1$.

Let us consider the quantity $\theta(n)$, collecting the observed data $x(n)$ and $y(n)$, then it is possible to write the following:

$$P_i(x(n),y(n))=P_i(\theta(n)=p(\theta(n)/E(n)=i),$$

$E(n)$ representing the state at the instant n.

If $E(0:N)$ denotes the series of states between the instant $n=0$ and the instant $n=N$, and if $\theta(0:N)$ denotes the observed data between the instant $n=0$ and the instant $n=N$, the probabilities of the sequence of states $E(0:N)$ corresponding to the sequence of states $E(0), E(1) \ldots E(N)$ can be expressed as:

$$p(E(0:N) \mid \theta(0:N-1)) \alpha p(E(0))$$

$$p(\theta(0)/E(0)) \prod_{n=1}^{N} p(E(n)/E(n-1)) p(\theta(n)/E(n))$$

For example, for the sequence E(0:N)={i, i, i, ..., i}, this probability can be expressed as:

$$p(E(0) = i) p(\theta(0) \mid E(0) = i) \prod_{n=1}^{N} p(E(n) = i \mid E(n-1) = i)) \quad (1)$$

$$p(\theta(n) \mid E(n) = i))$$

The estimated sequence of states E(0:N) can be that in which the probability is the highest. In practice, rather than considering all the possible sequences and for each one calculating its probability, it may be advantageous to use a Viterbi algorithm for estimating this sequence.

P(E(0)) denotes the probability associated with the initial state E(0). It is possible for example to choose an equiprobable distribution of each of the possible states when n=0.

p(θ(0)/E(0)) represents the probability of observing the data θ(0) at the instant E(0). This corresponds to the probability $P_i(x(n=0),y(n=0))$ with E(n)=i.

p(E(n)/E(n−1)) represents the probability of being in a state E(n) at the instant n, whereas the person was in a state E(n−1) at the instant n−1.

p(θ(n)/E(n)) represents the probability of observing the quantities θ(n) when the person is in the state E(n). This corresponds to the probability $P_i(x(n),y(n))$ with E(n)=i.

The probabilities p(E(n)/E(n−1)) correspond to probabilities of a transition from a state E(n−1) to a state E(n). These probabilities are indicated in the following embodiment table, adopting the notations E(n−1)=j and E(n)=i.

The series of states E(0) ... E(N) maximizing the expression (1) may be obtained using for example the Viterbi algorithm well known to those skilled in the art.

Thus:

1) by establishing, for each state E(n):
   the probability of observing the quantities θ(n) when the person is in the state E(n), denoted by p(θ(n)/E(n));
   the probability of a transition from a state E(n−1) to a state E(n), denoted by p(E(n)/E(n−1));

2) by establishing the probability associated with each state E(0); and 3) by obtaining observed quantities θ(n) at each instant n between n=0 and n=N, it is possible to obtain the most probable series of states E(0) .... E(N).

It is noted that, in the expression θ(n)={x(n), y(n)}, x(n) and y(n) are the so-called low-frequency and high-frequency components respectively of the signal S(n) measured by the motion sensor at the instant n.

In one embodiment, the probabilities P, of said hidden Markov model, for transitions between two successive states representing respectively one type of posture, are such that:

| P(jState/iState) | 1State (rest) | 2State (slight agitation) | 3State (trembling) | 4State (moderate agitation) | 5State (strong agitation) |
|---|---|---|---|---|---|
| 1State (rest) | 0.9900 | 0.0025 | 0.0025 | 0.0025 | 0.0025 |
| 2State (slight agitation) | 0.007 | 0.99 | 0.0010 | 0.0010 | 0.0010 |
| 3State (trembling) | 0.007 | 0.0010 | 0.99 | 0.0010 | 0.0010 |
| 4State (moderate agitation) | 0.007 | 0.0010 | 0.0010 | 0.99 | 0.0010 |
| 5State (strong agitation) | 0.007 | 0.0010 | 0.0010 | 0.0010 | 0.99 |

These values are particularly well suited for determining the activity of a person lying down.

According to one embodiment, the system includes display means.

Thus, the results may be displayed in real time or subsequently.

In one embodiment, said motion sensor comprises an accelerometer and/or a magnetometer and/or a gyroscope.

According to one embodiment, the system comprises fastening means suitable for being fastened to the wrist, to the torso or to the head of the person.

According to another aspect of the invention, a method is provided for determining the activity of a person lying down, comprising at least a step of configuring two processing pathways of signals at the output of at least one motion sensor substantially affixed to said person, wherein a first of said at least two processing pathways processes a first component comprising signals of low frequencies and a second processing pathway processes a second component of signals of high frequencies, said method further comprising:
   a first calculation step for calculating a first variable (x(n)) representing a temporal variation of said first component, for at least an axis of said motion sensor;
   a second calculation step for calculating a second variable (y(n)) comprising the Euclidean norm, along at least one measurement axis, of said second component; and
   an analysis step for determining an activity of said person as a function of time using a hidden Markov model having N states corresponding to N activities respectively,
   said analysis step combining sub-steps of calculating:
   conjoint probability density functions of said first and second variables, said probability density functions being defined for each state of the model in question; and
   probabilities of transitions between two successive states.

BRIEF DESCRIPTION OF THE FIGURES

The invention will be better understood by studying a few embodiments described by way of entirely non-limiting examples and illustrated by the appended drawings in which.

DETAILED DESCRIPTION

Figure 1:
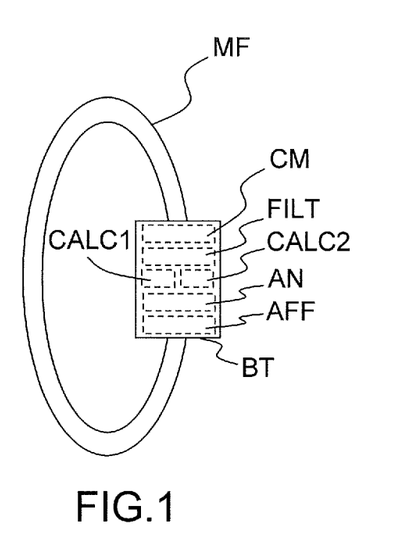
FIGS. 1 and 2 illustrate a system, according to one aspect of the invention.

FIG. 1 illustrates a system for determining the posture of a person, comprising at least one motion sensor CM having at least one measurement axis, provided with fastening means comprising, for example, a resilient element, for firmly connecting the motion sensor CM to a user. The motion sensor CM may be an accelerometer, a magnetometer or a gyroscope having one, two or three measurement axes.

The system comprises a filter FILT for selecting, for each measurement axis of the motion sensor CM, high frequencies HF above a first threshold S1 and low frequencies below a second threshold S2 equal to or below the first threshold S1. The system also comprises a first calculation module CALC1 for calculating a first value x representing the variation, between two different, for example successive, instants, along at least one measurement axis, of said low frequencies BF.

The system also comprises a second calculation module CALC2 for calculating a second value y equal to the average of the variances, along each measurement axis, of the high frequencies HF.

The way in which the first value x(n) and the second value y(n) are established, at each instant (n), is explained in more detail below.

The signal measured by an accelerometer at an instant n may be decomposed into two summed components: S(n)=SG(n)+SP(n), SG(n), representing the projection of the gravitational field and SP(n) representing the intrinsic acceleration of the person wearing the accelerometer.

By applying a low-pass filter to the signal S(n), the cutoff frequency being below 1 Hz, for example equal to 0.5 Hz, an estimate SG*(n) of SG(n) is obtained.

Thus, an estimate SP*(n) of SP(n) is such that SP*(n)=S(n)−SG*(n).

A first value, or low-frequency component, denoted by x(n), representing a variation of the signal SG* between different, for example successive, instants, i.e. SG*(n−1) and SG*(n), may then be defined. Thus, it may be stated that x(n) represents a temporal variation of the low-frequency signal of the accelerometer.

The following expression may be advantageously chosen:

$$x(n) = \sum_k SG_k^*(n) - SG_k^*(n-1),$$

the index k representing the axis (or axes) along which the component $S_k(n)$ of the signal S(n) was measured.

It is possible to determine x(n) using only a single component (for example the vertical axis) or a plurality of components $S_k(n)$ of the signal S(n).

It is also possible to define a second value, or high-frequency component y(n), of the signal S(n), this component being determined from SP*(n). According to a preferred embodiment, $y(n)=\|SP^*(n)\|^2$, this norm being calculated considering one or more axes.

Thus, it is possible to state that y(n) comprises the average of the variances, along at least one measurement axis, of the measured high-frequency signal.

Analysis means AN serve for determining an activity of a lying-down user, as a function of time, using a hidden Markov model having N states corresponding to N activities, respectively.

Thus, for each state i, probability density functions $P_{x,i}(n)$ and $P_{y,i}(n)$, are defined such that:

$$\begin{cases} P_{x,i}(x(n)) = \dfrac{1}{\sqrt{2\pi}\,\sigma_x} \cdot e^{-\frac{x(n)^2}{2\sigma_{x,i}^2}} \\ P_{y,i}(y(n)) = \dfrac{1}{\sqrt{2^k}\,\sigma_{y,i}^k \Gamma\!\left(\frac{k}{2}\right)} y(n)^{\frac{k}{2}-1} e^{-\frac{y(n)}{2\sigma_{y,i}^2}} \end{cases}$$

k representing the degree of freedom of the high-frequency component (HF) equal to the number of measurement axes taken into account by said motion sensor (CM);

$\sigma_x$ representing the square root of the variance of the first variable x, in the state of the hidden Markov model in question;

$\sigma_{y,i}$ being a quantity proportional to the time average of the variable y(n) in the state i, (for example, $\sigma_{y,i}$ is the time average of the variable y(n) divided by k); and Γ being the gamma function satisfying $$\Gamma\!\left(\frac{1}{2}\right) = \sqrt{\pi},\ \Gamma(1) = 1 \text{ and } \Gamma\!\left(n+1+\frac{1}{2}\right) = n\Gamma\!\left(n+\frac{1}{2}\right).$$

The system also includes a display screen AFF.

For example, the system comprises an accelerometer having one measurement axis and a fastening element for fastening the accelerometer to the user's wrist.

The analysis means AN are suitable for determining an activity of the lying-down user as a function of time using a hidden Markov model in at most five states chosen from a rest activity, a slight agitation activity, a trembling activity, a moderate agitation activity and a strong agitation activity.

The analysis means AN are suitable for determining an activity of the lying-down user from a set of predetermined pairs of values of first and second variances, defining movement classes. For example, the pairs of values $((\sigma_x[m]; \sigma_y[n])$ of first and second variances are suitable for satisfying the following conditions:

$$\begin{cases} n \in [0; n_{max}] \\ m \in [(0; m)_{max}] \\ n_{max} \leq 10 \\ m_{max} \leq 10 \\ n_{max} \times m_{max} \geq 6. \end{cases}$$

The analysis means AN are suitable for determining the probability density function of a state iState of the hidden Markov model by the following equation:

$$P_{iState}(x, y) = \sum_{n=0}^{n_{max}} \sum_{m=0}^{m_{max}} \alpha_{iState,m+(n_{max}+1)n} P_{BF(\sigma_x[m])}(x) P_{HF(\sigma_y[n])}(y)$$

in which:

$\alpha_{iState,j}$ is a real coefficient between 0 and 1;

$$\sum_{j=0}^{j_{max}} \alpha_{iState,j} = 1$$

and $$j_{max} = (m_{max} + 1)(n_{max} + 1) - 1.$$

The movement classes are, for example, eighteen in number and are defined by:
$\sigma_x[0]=5\times10^{-3}$, $\sigma_x[1]=1.8\times10^{-2}$, $\sigma_x[2]=3.5\times10^{-2}$, $\sigma_x[3]=5.5\times10^{-2}$, $\sigma_x[4]=8\times10^{-2}$, $\sigma_x[5]=1\times10^{-1}$, $\sigma_y[0]=1\times10^{-2}$, $\sigma_y[1]=3\times10^{-2}$ and $\sigma_y[2]=8\times10^{-2}$.

The real coefficients ($\alpha_{iState,j}$) are defined by the following embodiment table:

| | iState | | | | |
|---|---|---|---|---|---|
| Class | 1State (rest) | 2State (slight agitation) | 3State (trembling) | 4State (moderate agitation) | 5State (strong agitation) |
| 0 | 0.2564 | 0 | 0 | 0 | 0 |
| 1 | 0.0513 | 0.0526 | 0 | 0 | 0 |
| 2 | 0.02564 | 0 | 0.04 | 0 | 0 |
| 3 | 0.2564 | 0.1579 | 0.04 | 0 | 0 |
| 4 | 0.0513 | 0.2632 | 0.16 | 0 | 0 |
| 5 | 0 | 0.0526 | 0.20 | 0 | 0 |
| 6 | 0.2564 | 0.1579 | 0.04 | 0 | 0 |
| 7 | 0.0513 | 0.2632 | 0.16 | 0.0926 | 0 |
| 8 | 0 | 0.0526 | 0.20 | 0.0926 | 0 |
| 9 | 0.0256 | 0 | 0 | 0.0370 | 0 |
| 10 | 0 | 0 | 0 | 0.1852 | 0 |
| 11 | 0 | 0 | 0.16 | 0.1852 | 0 |
| 12 | 0.0256 | 0 | 0 | 0.037 | 0.0556 |
| 13 | 0 | 0 | 0 | 0.1852 | 0.0556 |
| 14 | 0 | 0 | 0 | 0.1852 | 0.0556 |
| 15 | 0 | 0 | 0 | 0 | 0.2778 |
| 16 | 0 | 0 | 0 | 0 | 0.2778 |
| 17 | 0 | 0 | 0 | 0 | 0.2778 |

The probabilities P, of said hidden Markov model, for transitions between two states representing respectively one type of posture, can be such that:

| P(jState/iState) | 1State (rest) | 2State (slight agitation) | 3State (trembling) | 4State (moderate agitation) | 5State (strong agitation) |
|---|---|---|---|---|---|
| 1State (rest) | 0.9900 | 0.0025 | 0.0025 | 0.0025 | 0.0025 |
| 2State (slight agitation) | 0.007 | 0.99 | 0.0010 | 0.0010 | 0.0010 |
| 3State (trembling) | 0.007 | 0.0010 | 0.99 | 0.0010 | 0.0010 |
| 4State (moderate agitation) | 0.007 | 0.0010 | 0.0010 | 0.99 | 0.0010 |
| 5State (strong agitation) | 0.007 | 0.0010 | 0.0010 | 0.0010 | 0.99 |

For example, the motion sensor CM may comprise an accelerometer and/or a magnetometer and/or a gyroscope.

Figure 2:
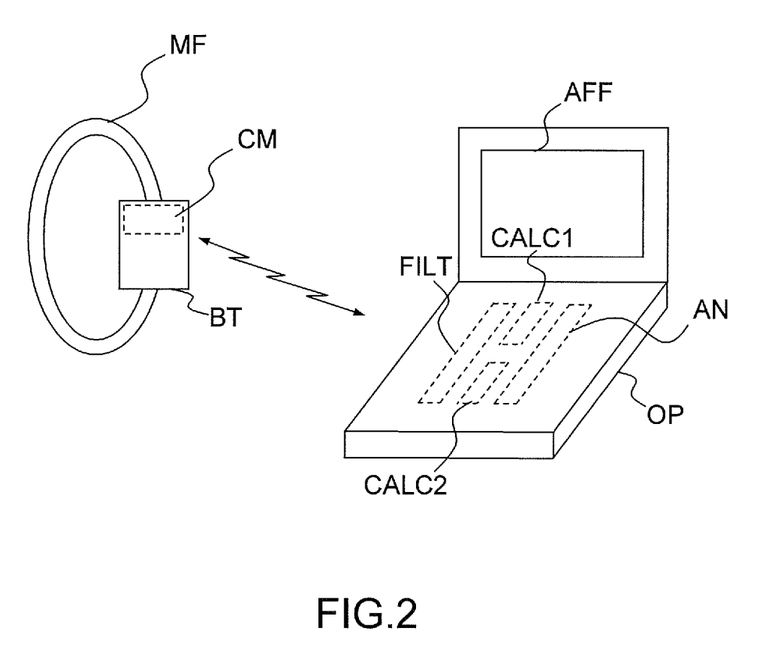

FIG. 2 illustrates an alternative embodiment in which, unlike the embodiment illustrated in FIG. 1, for which the motion sensor CM and the other elements are incorporated into a casing BT, elements of the system may be externalized, for example in a portable computer OP.

The analysis module AN determines, from the input signals and from the hidden Markov model as defined, the most probable sequence of states (postures), using conventional methods, for example by calculating, for the set of possible sequences of states, the associated probability taking into account the observed signal and keeping the most probable sequence, as described for example in the document "An introduction to hidden Markov models" by L. R. Rabiner and B. H. Juang, IEEE ASSP Magazine, January 1986, or in the book "Inference in Hidden Markov Models" by Cappé Moulines and Ryden, Springer (from the "Springer series in statistics" series).

Figure 3:
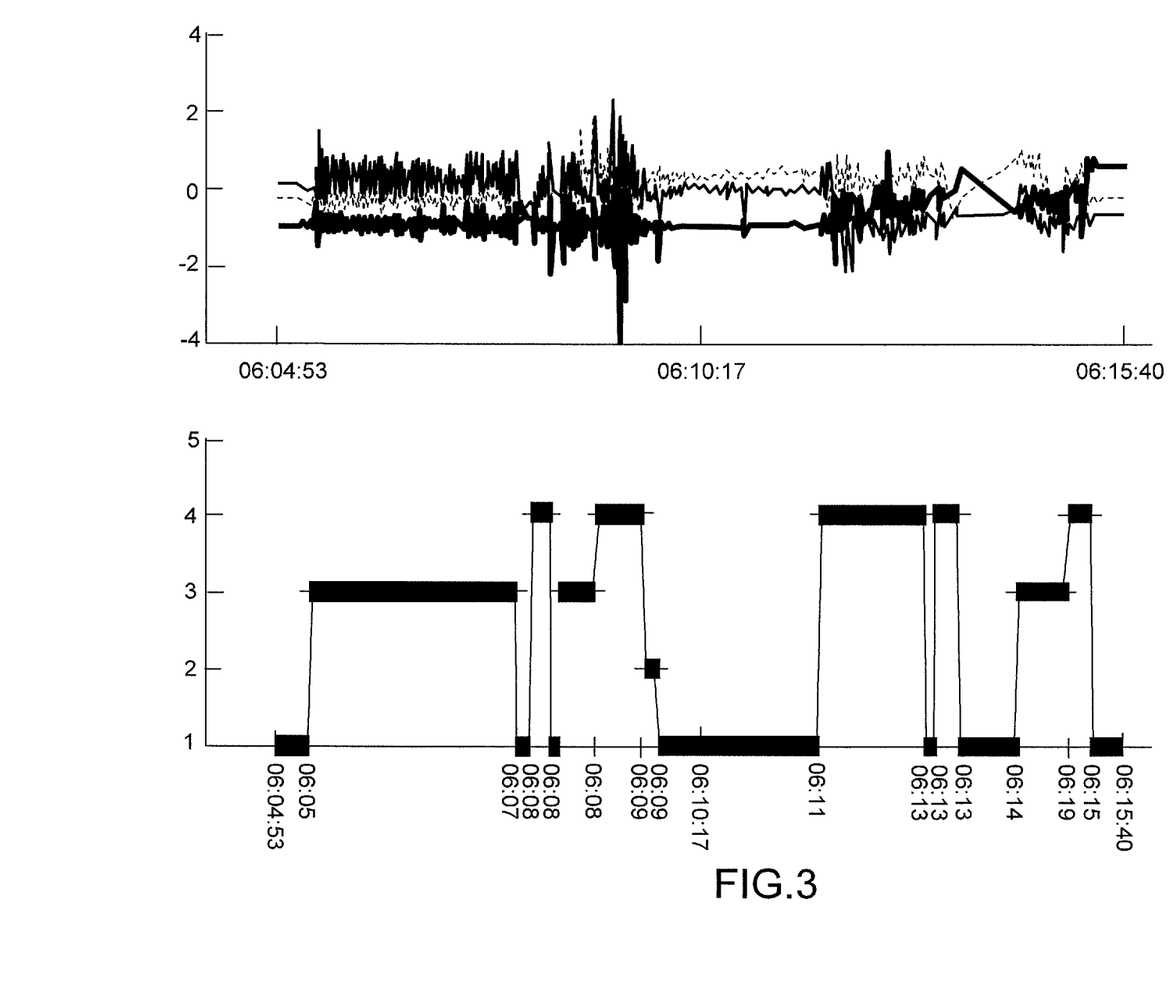
FIG. 3 illustrates an example of a recording by a system according to one aspect of the invention.

FIG. 3 illustrates an example of a recording from a person using an embodiment system shown in FIGS. 1 and 2, comprising a triaxial accelerometer, and the results provided by the system.

This portion of a recording from a lying-down user was obtained over a period of around ten minutes.

The system indicates that the lying-down user was in a rest activity (1State) from 6 h 04 min 53 s to 6 h 05 min 18 s, in a trembling activity (3State) from 6 h 05 min 18 s to 6 h 07 min 57 s, in a rest activity (1State) from 6 h 07 min 57 s to 6 h 08 min 10 s, in a moderate agitation activity (4State) from 6 h 08 min 10 s to 6 h 08 min 22 s, in a rest activity (1State) from 6 h 08 min 22 s to 6 h 08 min 32 s, in a trembling activity (3State) from 6 h 08 min 32 s to 6 h 08 min 57 s, in a moderate agitation activity (4State) from 6 h 08 min 57 s to 6 h 09 min 33 s, in a slight agitation activity (2State) from 6 h 09 min 33 s to 6 h 09 min 47 s, in a rest activity (1State) from 6 h 09 min 47 s to 6 h 11 min 49 s, in a moderate agitation activity (4State) from 6 h 11 min 49 s to 6 h 13 min 07 s, in a rest activity (1State) from 6 h 13 min 07 s to 6 h 13 min 19 s, in a moderate agitation activity (4State) from 6 h 13 min 19 s to 6 h 13 min 35 s, in a rest activity (1State) from 6 h 13 min 35 s to 6 h 14 min 22 s, in a trembling activity (3State) from 6 h 14 min 22 s to 6 h 14 min 59 s, in a moderate agitation activity (4State) from 6 h 14 min 59 s to 6 h 15 min 18 s, and in a rest activity (1State) from 6 h 15 min 18 s to 6 h 15 min 40 s.

The present invention makes it possible, for a low cost and with improved accuracy, to determine, in real time or subsequently, the posture of a person by accurately determining the changes in posture. Such an invention makes it possible to analyze the activity of a sleeping person, or to detect a nocturnal epileptic fit, with improved accuracy and for low cost.

The examples provided are merely exemplary, as a matter of application specific to design choice, and should not be construed to limit the scope of the invention in any way. Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

The invention claimed is:

1. A system for determining activity of a person lying down, comprising at least two processing pathways of signals at an output of at least one motion sensor substantially affixed to said person, wherein a first of said at least two processing pathways processes a first component comprising signals of low frequencies and a second processing pathway processes a second component of signals of high frequencies, said system further comprising:
   one or more processors;
   a first calculation module configured to calculate, using said one or more processors, a first variable representing a temporal variation of said first component, for at least an axis of said motion sensor;

a second calculation module configured to calculate, using said one or more processors, a second variable comprising a Euclidean norm, along at least one measurement axis, of said second component; and an analysis module configured to determine, using said one or more processors, an activity of said person as a function of time using a hidden Markov model having N states corresponding to N activities respectively, said analysis module being configured for combining: conjoint probability density functions of said first and second variables, said probability density functions being defined for each state of the model; and probabilities of transitions between at least two successive states.

2. The system of claim 1, wherein the probability density functions associated with each state are a function of a product of at least one first probability density function of said first variable multiplied by at least one second probability density function associated with said second variable.

3. The system of claim 2, wherein each conjoint probability density function (P(x,y)) comprises a product of at least one probability density function ($P_{x,i}(n)$) for obtaining the first variable (x) and of at least one probability density function ($P_{y,i}(n)$) for obtaining the second variable (y), and said probability density functions ($P_{x,i}(n)$ and $P_{y,i}(n)$) are defined by the following expressions:

$$\begin{cases} P_{x,i}(x(n)) = \dfrac{1}{\sqrt{2\pi}\,\sigma_x} \cdot e^{-\frac{x(n)^2}{2\sigma_{x,i}^2}} \\ P_{y,i}(y(n)) = \dfrac{1}{\sqrt{2^k}\,\sigma_{y,i}^k\,\Gamma\left(\frac{k}{2}\right)} y(n)^{\frac{k}{2}-1} e^{-\frac{y(n)}{2\sigma_{y,i}^2}} \end{cases}$$

wherein:

k represents a degree of freedom of the second component equal to the number of measurement axes taken into account by said motion sensor;

$\sigma_x$ represents a square root of a variance of the first variable x, in the state of the hidden Markov model in question;

$\sigma_{y,i}$ is a quantity proportional to a time average of the second variable y(n) in the state i; and $\Gamma$ is a gamma function satisfying $$\Gamma\left(\frac{1}{2}\right) = \sqrt{\pi},\ \Gamma(1) = 1\ \text{and}\ \Gamma\left(n+1+\frac{1}{2}\right) = n\Gamma\left(n+\frac{1}{2}\right).$$

4. The system of claim 1, wherein said analysis module is configured to determine an activity of the lying-down person as a function of time using a hidden Markov model in at most five states chosen from a rest activity, a slight agitation activity, a trembling activity, a moderate agitation activity, and a strong agitation activity.

5. The system of claim 4, wherein said analysis module is configured to determine an activity of the lying-down person from a set of predetermined pairs of values (($\sigma_x[m]$; $\sigma_y[n]$)) of first and second variances, defining motion classes ($\sigma_x$, $\sigma_y$).

6. The system of claim 5, wherein said pairs of values (($\sigma_x[m]$; $\sigma_y[n]$)) of first and second variances are configured for satisfying the following conditions:

$$\begin{cases} n \in [0;\ n_{max}] \\ m \in [(0;\ m)_{max}] \\ n_{max} \le 10 \\ m_{max} \le 10 \\ n_{max} \times m_{max} \ge 6. \end{cases}$$

7. The system of claim 6, wherein said analysis module is configured to determine the conjoint probability density function of a state of said hidden Markov model through the following equation:

$$P(x(n), y(n)\,|\,\text{State} = i) = P_{iState}(x(n), y(n))$$

$$= \sum_{n=0}^{n_{max}} \sum_{m=0}^{m_{max}} \alpha_{iState,m+(m_{max}+1)n} P_{x(\sigma_x[m])}$$

$$(x(n)) P_{y(\sigma_y[n])}(y(n)).$$

in which:

iState represents a state of the hidden Markov model;

$\alpha_{iState,j}$ is a weighting coefficient; and $$\sum_{n=0}^{n_{max}} \sum_{m=0}^{m_{max}} \alpha_{iState,m+(m_{max}+1)n} = 1.$$

8. The system of claim 7, wherein said motion classes are eighteen in number and are defined by:

$\sigma_x[0]=5\times10^{-3}$, $\sigma_x[1]=1.8\times10^{-2}$, $\sigma_x[2]=3.5\times10^{-2}$, $\sigma_x[3]=5.5\times10^{-2}$, $\sigma_x[4]=8\times10^{-2}$, $\sigma_x[5]=1\times10^{-1}$, $\sigma_y[0]=1\times10^{-2}$, $\sigma_y[1]=3\times10^{-2}$ and $\sigma_y[2]=8\times10^{-2}$.

9. The system of claim 8, wherein said weighting coefficients ($\alpha_{iState,j}$) are defined by the following table:

| | iState | | | | |
|---|---|---|---|---|---|
| Class | 1State (rest) | 2State (slight agitation) | 3State (trembling) | 4State (moderate agitation) | 5State (strong agitation) |
| 0 | 0.2564 | 0 | 0 | 0 | 0 |
| 1 | 0.0513 | 0.0526 | 0 | 0 | 0 |
| 2 | 0.02564 | 0 | 0.04 | 0 | 0 |
| 3 | 0.2564 | 0.1579 | 0.04 | 0 | 0 |
| 4 | 0.0513 | 0.2632 | 0.16 | 0 | 0 |
| 5 | 0 | 0.0526 | 0.20 | 0 | 0 |
| 6 | 0.2564 | 0.1579 | 0.04 | 0 | 0 |
| 7 | 0.0513 | 0.2632 | 0.16 | 0.0926 | 0 |
| 8 | 0 | 0.0526 | 0.20 | 0.0926 | 0 |
| 9 | 0.0256 | 0 | 0 | 0.0370 | 0 |
| 10 | 0 | 0 | 0 | 0.1852 | 0 |
| 11 | 0 | 0 | 0.16 | 0.1852 | 0 |
| 12 | 0.0256 | 0 | 0 | 0.037 | 0.0556 |
| 13 | 0 | 0 | 0 | 0.1852 | 0.0556 |
| 14 | 0 | 0 | 0 | 0.1852 | 0.0556 |
| 15 | 0 | 0 | 0 | 0 | 0.2778 |
| 16 | 0 | 0 | 0 | 0 | 0.2778 |
| 17 | 0 | 0 | 0 | 0 | 0.2778 |

10. The system of claim 9, wherein the probabilities P(jState/iState) of said hidden Markov model, for transitions between two states representing respectively one type of posture, are such that:

| P(jState/ iState) | 1State (rest) | 2State (slight agitation) | 3State (trembling) | 4State (moderate agitation) | 5State (strong agitation) |
| --- | --- | --- | --- | --- | --- |
| 1State (rest) | 0.9900 | 0.0025 | 0.0025 | 0.0025 | 0.0025 |
| 2State (slight agitation) | 0.007 | 0.99 | 0.0010 | 0.0010 | 0.0010 |
| 3State (trembling) | 0.007 | 0.0010 | 0.99 | 0.0010 | 0.0010 |
| 4State (moderate agitation) | 0.007 | 0.0010 | 0.0010 | 0.99 | 0.0010 |
| 5State (strong agitation) | 0.007 | 0.0010 | 0.0010 | 0.0010 | 0.99 |

11. The system of claim 1, further including a display.

12. The system of claim 1, wherein said motion sensor comprises at least one of an accelerometer, a magnetometer and a gyroscope.

13. The system of claim 1, further comprising fastening means configured for being fastened to the wrist, to the torso or to the head of the person.

14. A method for determining activity of a person lying down, comprising at least a step of configuring two processing pathways of signals at an output of at least one motion sensor substantially affixed to said person, wherein a first of said at least two processing pathways processes a first component comprising signals of low frequencies and a second processing pathway processes a second component of signals of high frequencies, said method further comprising:
- a first calculation step for calculating a first variable representing a temporal variation of said first component, for at least an axis of said motion sensor;
- a second calculation step for calculating a second variable comprising a Euclidean norm, along at least one measurement axis, of said second component; and
- an analysis step for determining an activity of said person as a function of time using a hidden Markov model having N states corresponding to N activities respectively, said analysis step comprising sub-steps of calculating:
- conjoint probability density functions of said first and second variables, said probability density functions being defined for each state of the model; and
- probabilities of transitions between at least two successive states.

15. The method of claim 14, wherein the conjoint probability density functions are established by determining, for each state:
- first probability density functions of a first value; and
- second probability density functions of a second value.

* * * * *